United States Patent
Doering

(10) Patent No.: US 10,632,328 B2
(45) Date of Patent: Apr. 28, 2020

(54) COSMETIC AGENTS CONTAINING A COMBINATION OF AT LEAST TWO DIFFERENT ACTIVE INGREDIENTS

(71) Applicant: Henkel AG & Co. KGaA, Duesseldorf (DE)

(72) Inventor: Thomas Doering, Dormagen (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 0 days.

(21) Appl. No.: 15/691,949

(22) Filed: Aug. 31, 2017

(65) Prior Publication Data

US 2018/0117368 A1 May 3, 2018

(30) Foreign Application Priority Data

Oct. 27, 2016 (DE) .................. 10 2016 221 154

(51) Int. Cl.
| | | |
|---|---|---|
| *A61Q 15/00* | (2006.01) | |
| *A61K 8/36* | (2006.01) | |
| *A61K 8/34* | (2006.01) | |
| *A61K 8/28* | (2006.01) | |
| *A61K 8/26* | (2006.01) | |
| *A61K 8/37* | (2006.01) | |

(52) U.S. Cl.
CPC .............. *A61Q 15/00* (2013.01); *A61K 8/26* (2013.01); *A61K 8/28* (2013.01); *A61K 8/345* (2013.01); *A61K 8/36* (2013.01); *A61K 8/375* (2013.01)

(58) Field of Classification Search
None
See application file for complete search history.

(56) References Cited

U.S. PATENT DOCUMENTS

| | | | | |
|---|---|---|---|---|
| 5,538,718 A * | 7/1996 | Aul | ............... | A61K 8/02 424/401 |
| 2003/0194415 A1* | 10/2003 | Wang | ............... | A01N 33/24 424/400 |
| 2004/0258721 A1* | 12/2004 | Bauer | ............... | A61K 8/0229 424/401 |
| 2007/0031361 A1* | 2/2007 | Herrmann | ............... | A61K 8/8111 424/70.11 |
| 2009/0208437 A1* | 8/2009 | Woehrmann | ............... | A61K 8/0229 424/65 |
| 2012/0258058 A1* | 10/2012 | Herrmann | ............... | A61K 8/34 424/59 |
| 2012/0288462 A1* | 11/2012 | Lebok | ............... | A61K 8/0229 424/64 |
| 2016/0279044 A1* | 9/2016 | Sirichandra | ............... | A61K 8/375 |
| 2018/0168954 A1* | 6/2018 | Millet | ............... | A61K 8/25 |

FOREIGN PATENT DOCUMENTS

| | | | |
|---|---|---|---|
| DE | 19516705 A1 | | 11/1996 |
| DE | 19631003 A1 | | 2/1998 |
| EP | 0742004 | * | 11/1996 |
| EP | 0742004 B1 | | 11/1996 |
| EP | 0775478 A1 | | 5/1997 |
| EP | 0982024 A2 | | 3/2000 |
| EP | 2170796 B1 | | 9/2012 |
| WO | WO 2014098267 | * | 6/2014 |

OTHER PUBLICATIONS

Intellectual Property Office, Search Report under Section 17(5) for United Kingdom Patent Application No. GB1714762.0 dated May 18, 2018.
Substance Record for SID 175427393 retrieved on May 14, 2018 from the internet at: https://pubchem.ncbi.nlm.nih.gov/substance/175427393/version/1#section=Top.

* cited by examiner

*Primary Examiner* — Robert A Wax
*Assistant Examiner* — Danah Al-Awadi
(74) *Attorney, Agent, or Firm* — Lorenz & Kopf, LLP

(57) ABSTRACT

Cosmetic agents including a combination of at least two different active ingredients are provided herein. In one example, a cosmetic agent includes 2-butyloctanoic acid and at least one polyglyceryl-3 ester of a fatty acid in a cosmetically acceptable carrier.

3 Claims, No Drawings

US 10,632,328 B2

COSMETIC AGENTS CONTAINING A COMBINATION OF AT LEAST TWO DIFFERENT ACTIVE INGREDIENTS

CROSS-REFERENCE TO RELATED APPLICATION

This application claims priority to Patent Application No. DE102016221154.4, filed Oct. 27, 2016, which is incorporated herein by reference in its entirety.

TECHNICAL FIELD

The present application pertains to cosmetic agents which contain a combination of at least two active ingredients. These cosmetic agents have an excellent deodorizing effect which also persists over a long period of time.

Furthermore, the present disclosure relates to a method for reducing and/or avoiding body odor caused by perspiration, in which a cosmetic agent as contemplated herein is applied to the skin and remains there for at least one hour.

Finally, the present disclosure relates to the use of a cosmetic agent as contemplated herein for reducing and/or avoiding body odor caused by the perspiration.

BACKGROUND

Eccrine and apocrine sweat glands are found in the human armpit. While the eccrine glands produce an aqueous secretion in response to heat, the apocrine glands can secrete a viscous secretion in response to stress. This apocrine sweat is a complex mixture containing, among other things, steroids, cholesterol and other fats and approx. 10% proteins. Bacterial decomposition of the contents of the apocrine sweat produces unpleasant body odor under the armpit from the initially odorless secretion.

The decomposition products of apocrine perspiration, which contribute significantly to body odor, in particular axillary body odor, can be divided into three classes: the first class is short chain $C_4$-$C_{10}$ fatty acids which can be linear, branched, saturated and unsaturated (for example isovaleric acid, 3-methyl-2-hexenoic acid, 3-hydroxy-3-methylhexanoic acid), the second class forming short-chain linear or branched sulfanyl alcohols, the third class includes different steroid hormones and their metabolic products. (e.g., 5-α-androstenol and 5-α-androstenone).

Body odor can thus be combated by avoiding the bacterial breakdown of the sweat or by using perfume to cover the body odor. In order to avoid the bacterial degradation of the sweat, the prior art uses antimicrobial substances which reduce the number of perspiration-destroying bacteria on the skin by killing or inhibiting the growth of these bacteria. Furthermore, active ingredients are known which reduce and/or prevent the formation of decomposition products by the blocking of bacterial enzymes. In addition, it is known to absorb the volatile decomposition products by physical and/or chemical interaction and in this way to avoid unpleasant body odor. In addition, the formation of body sweat can also be reduced by the use of antiperspirant active ingredients so that less or no decomposition products can be formed by the perspiration-decomposing bacteria. There is, however, still a need for cosmetic agents which have both a high and a long-lasting deodorizing effect.

The use of 2-butyloctanoic acid as a deodorizing agent is known from the prior art. European patent EP 0 742 004 B1 discloses the use of dialkyl-substituted acetic acids such as 2-butyloctanoic acid as antibacterial, antimycotic or antiviral active ingredients.

Active ingredient combinations of dialkyl-substituted acetic acids having one or more substances selected from the group of monoglycerol monoalkyl ethers, the diglycerol monoalkyl ethers, the triglycerol monoalkyl ethers, the monoglycerol dialialkyl ethers, the diglycerol dialkyl ethers and the triglycerinedialkyl ethers are disclosed in EP 1 461 004 B1.

The assignee of the prior art mentioned above distributes deodorants and antiperspirants containing 2-butyloctanoic acid. Polyglyceryl-2 caprates or polyglyceryl-2 dipolyhydroxystearates are used as emulsifiers, for example, in the market products.

BRIEF SUMMARY

Cosmetic agents and methods of using cosmetic agents are provided herein. In an exemplary embodiment, a cosmetic agent includes, in a cosmetically acceptable carrier, 2-butyloctanoic acid and at least one polyglyceryl-3 ester of a fatty acid.

DETAILED DESCRIPTION

The following detailed description is merely exemplary in nature and is not intended to limit the disclosure or the application and uses of the subject matter as described herein. Furthermore, there is no intention to be bound by any theory presented in the preceding background or the following detailed description.

The object of the present disclosure was to provide cosmetic agents which lead to a good and long-lasting effect against body odor. Furthermore, the occurrence of skin rashes and/or skin irritations during and/or after application of the cosmetic agent as contemplated herein is to be avoided. In addition, the cosmetic agents should have high storage stability and good cosmetic properties.

It has now surprisingly been found that the use of a combination of 2-butyloctanoic acid with a polyglyceryl-3 fatty acid ester not only results in a specific control of the odor-causing bacteria, but that an unexpectedly long-lasting deodorizing effect is also achieved. Through the synergistic effect of the two components mentioned above of the cosmetic agents as contemplated herein, the amount of active ingredients can be reduced without adversely affecting the deodorizing effect. Because of the reduced amount of active ingredients, the cosmetic agents as contemplated herein are free of irritation and sensitization. Furthermore, the use of the active ingredient combination does not have a negative effect on the storage stability of the cosmetic agents as contemplated herein, so that these agents have excellent storage stability. Finally, these agents have good cosmetic properties.

A first subject of the present application is therefore a cosmetic agent containing, in a cosmetically acceptable carrier,
a) 2-butyloctanoic acid and
b) at least one polyglyceryl-3 ester of a fatty acid.

Using a combination of 2-butyloctanoic acid with a polyglyceryl-3 fatty acid ester achieves an excellent reduction of the body odor caused by perspiration, in particular of the body odor under the armpit, in particular under the armpit. Moreover, it has been found that the combination of the two components a) and b) of the cosmetic agents as contemplated herein has a synergistic increase in deodorizing performance so that the amount of active ingredients can be reduced without adversely affecting the deodorizing effect. The cosmetic agents as contemplated herein have improved skin compatibility due to the reduced amount of active ingredients. Moreover, the cosmetic properties of the cosmetic agents as contemplated herein can be improved by using the above-mentioned combination of active ingredients. Finally, the use of components a) and b) does not lead to a negative effect on the storage stability of the cosmetic agents as contemplated herein.

The term "fatty acid", as used in the context of the present disclosure, is to be understood to mean aliphatic carboxylic acids which have unbranched or branched carbon radicals having 4 to 40 carbon atoms. The fatty acids used in the context of the present disclosure can be both naturally occurring and synthetically produced fatty acids. Furthermore, the fatty acids can be mono- or polyunsaturated.

In the present case, unless otherwise indicated, the percentage by weight refers to the total weight of the cosmetic agents as contemplated herein, wherein the sum of all the ingredients of the agents as contemplated herein is 100% by weight. Furthermore, unless otherwise stated, the weight % refers to the amount of the respective component in the propellant-free cosmetic agent, so that the amount of any propellant present is not taken into account in the calculation of the total weight of the cosmetic agents.

The cosmetic agent contains the components a) and b) in a cosmetically acceptable carrier. This preferably comprises at least one component selected from water, a $C_1$-$C_4$ alcohol, a cosmetic oil which is liquid under normal conditions, and mixtures thereof. The cosmetic oils which are liquid under normal conditions are immiscible with water and are neither odoriferous substances nor essential oils. For the purposes of the present application, "standard conditions" are a temperature of 20° C. and a pressure of 1.013 hPa.

Suitable cosmetic carriers are, for example, aqueous or aqueous-alcoholic carriers. In the following, carriers are understood to be those which contain more than 5.0% by weight of water or more than about 5.0% by weight of water and at least one $C_1$-$C_4$ alcohol, in each case based on the total weight of the cosmetic agent. Aqueous carriers preferably contain free water in a total amount of from about 10 to about 96% by weight, preferably from about 15 to about 80% by weight, more preferably from about 30 to about 70% by weight, in particular from about 40 to about 60% by weight, based on the total weight of the cosmetic agent. In aqueous-alcoholic carriers, ethanol is preferably used in a total amount of from about 0.1 to about 50% by weight, preferably from about 0.5 to about 30% by weight, more preferably from about 1.0 to about 20% by weight, in particular of from about 1.0 to about 9.0% by weight, based on the total weight of the cosmetic agent.

The aqueous and aqueous-alcoholic carriers mentioned above may additionally contain at least one ($C_2$-$C_6$) alkyl alcohol having 2 or 3 hydroxyl groups, in particular 1,2-propylene glycol, 1,3-propylene glycol, glycerin and 1,3-butylene glycol.

However, it is also possible to provide an anhydrous cosmetic carrier to be used. As contemplated herein, anhydrous carriers are understood to mean carriers which contain free water in a total amount less than about 5.0% by weight, preferably less than about 4.0% by weight, more preferably less than about 3.0% by weight, in particular about 0% by weight, based on the total weight of the cosmetic agent. For the purposes of the present disclosure, "free water" is understood to mean water which is different from water of crystallization, water of hydration or similar molecularly bound water of the components used. However, in the calculation of the total amount of free water, water of crystallization, water of hydration or similar molecularly bound water of the components used are not taken into account.

In this context, alcoholic media are used in particular as cosmetically acceptable carriers. In particular, the lower alcohols having 1 to 4 carbon atoms, customarily used for cosmetic purposes, for example ethanol and isopropanol, are included as alcohols. Alcoholic carriers preferably contain ethanol in a total amount of from about 20 to about 95% by weight, more preferably from about 25 to about 65% by weight, in particular from about 25 to about 60% by weight, based on the total weight of the cosmetic agent.

Furthermore, it is particularly preferred in this context to use liquid cosmetic oils as cosmetic carriers. These cosmetic oils may be selected from the group of (i) volatile non-silicone oils, in particular liquid paraffin oils and isoparaffin oils such as isodecane, isoundecane, isododecane, isotridecane, isotetradecane, isopentadecane, isohexadecane and isoeicosane; (ii) non-volatile, non-silicone oils, in particular the esters of linear or branched, saturated or unsaturated $C_{2-30}$ fatty alcohols having linear or branched, saturated or unsaturated $C_{2-30}$ fatty acids, which may be hydroxylated, the $C_8$-$C_{22}$ fatty alcohol esters of monovalent or polyvalent $C_2$-$C_7$ hydroxycarboxylic acids, the dicarboxylic acid esters of linear or branched $C_2$-$C_{10}$ alkanols, the addition products of ethylene oxide and/or propylene oxide with mono- or polyhydric $C_{3-22}$ alkanols, which may be esterified, the symmetrical, asymmetric or cyclic esters of carbonic acid with fatty alcohols, the esters of dimers of unsaturated $C_{12-22}$ fatty acids having monovalent, linear, branched and cyclic $C_{2-18}$ alkanols or $C_{2-6}$ alkanols, the benzoic acid esters of linear or branched $C_{8-22}$ alkanols, such as benzoic acid $C_{12-15}$ alkyl esters and benzoic acid isostearyl esters and benzoic acid octyldodecyl esters, the synthetic hydrocarbons, such as polyisobutene and polydecenes, the alicyclic hydrocarbons; and (iii) mixtures thereof.

The term "volatile cosmetic oil" refers, as contemplated herein, to cosmetic oils which have a vapor pressure of about 2.66 Pa to about 40,000 Pa (0.02 to 300 mm Hg) at 20° C. and an ambient pressure of about 1.013 hPa, preferably of from about 10 to about 12,000 Pa 0.1 to 90 mm Hg), more preferably from about 13 to about 3,000 Pa (from about 0.1 to about 23 mm Hg), in particular from about 15 to about 500 Pa (0.1 to 4 mm Hg). Furthermore, for the purposes of the present disclosure, the term "non-volatile cosmetic oils" is understood to mean cosmetic oils which have a vapor pressure of less than about 2.66 Pa (0.02 mm Hg) at 20° C. and an ambient pressure of 1.013 hPa.

As contemplated herein, it is furthermore preferred to use mixtures of the cosmetic oils mentioned above, in particular non-volatile and volatile cosmetic oils, since in this way parameters such as skin feel, visibility of the residue and stability of the cosmetic agent as contemplated herein are adjusted and the agent can thus be better adapted to the needs of the consumers.

In the context of the present disclosure, it is preferred when the cosmetic oil which is liquid at 20° C. and 1.013 hPa is used in a total amount of from about 1.0 to about 98% by weight, preferably from about 2.0 to about 95% by weight, more preferably from about 5 to about 70% by weight, still more preferably from about 10 to about 60% by weight, in particular from about 15 to about 50% by weight, based on the total weight of the cosmetic agent.

The cosmetic agent as contemplated herein contains 2-butyloctanoic acid as a first essential component a):

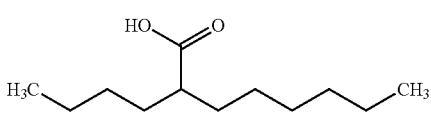

This is preferably used within a certain range of amounts. Preferred agents as contemplated herein, based on their weight, include from about 0.01 to about 1% by weight, preferably from about 0.02 to about 0.8% by weight, more preferably from about 0.03 to about 0.7% by weight, particularly preferably from about 0.04 to about 0.6% by weight and in particular from about 0.05 to about 0.5% by weight, of 2-butyloctanoic acid.

The cosmetic agent as contemplated herein contains at least one polyglyceryl-3 ester of a fatty acid as a second essential constituent b). These can be described by the formula

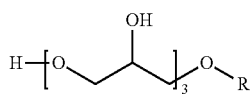

in which R stands for the acyl radical of a fatty acid.

Preferred agents as contemplated herein are wherein they contain at least one compound from the group of polyglyceryl-3 caprylate, polyglyceryl-3 caprate, polyglyceryl-3 laurate, polyglyceryl-3 myristate, polyglyceryl-3 palmitate, polyglyceryl-3 stearate, polyglyceryl-3 arachinate, polyglyceryl-3 behenate, polyglyceryl-3 palmitoleate, polyglyceryl-3 oleate, polyglyceryl-3 linolate.

This/these compound(s) is/are also preferably used within a certain range of amounts. Preferred agents as contemplated herein, based on their weight, are from about 0.1 to about 2.0% by weight, preferably from about 0.15 to about 1.5% by weight, more preferably from about 0.2 to about 1.0 by weight, particularly preferably from about 0.25 to about 0.8% by weight and in particular from about 0.3 to about 0.7% by weight, of a compound(s) selected from the group of polyglyceryl-3 caprylate, polyglyceryl-3 caprate, polyglyceryl-3 laurate, polyglyceryl-3 myristate, polyglyceryl-3 palmitate, polyglyceryl 3-stearate, polyglyceryl-3 arachinate, polyglyceryl-3 behenate, polyglyceryl-3 palmitoleate, polyglyceryl-3 oleate, polyglyceryl-3 linoleate.

Very particularly preferred cosmetic agents as contemplated herein contain, based on their weight, from about 0.1 to about 2.0% by weight, preferably from about 0.15 to about 1.5% by weight, more preferably from about 0.2 to about 1.0% by weight, particularly preferably from about 0.25 to about 0.8% by weight and in particular from about 0.3 to about 0.7% by weight of polyglyceryl-3 caprylate:

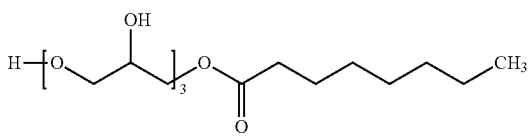

Preferably, if the total sum of components a) and b) is also within narrow ranges of quantities, preferred cosmetic agents as contemplated herein include the total amount of ingredients a) and b), based on the weight of the agent, is from about 0.25 to about 2.5% by weight, preferably from about 0.4 to about 2% by weight, more preferably from about 0.5 to about 1.5% by weight, particularly preferably from about 0.6 to about 1.0% by weight and in particular from about 0.7 to about 0.9% by weight.

The cosmetic agents as contemplated herein can contain further deodorizing and/or perspiration-inhibiting substances. Preferred cosmetic agents as contemplated herein are wherein they additionally contain one or more active ingredients selected from the group of triethyl citrate, 3-[(2-ethylhexyl)oxy]-1,2-propanediol, 2-benzylheptanol, phenoxyethanol, cocamidopropyl PG dimonium chloride phosphate, 1,2-hexanediol, 1,2-octanediol, 1,2-decanediol, tropolone, silver lactate, magnesium oxide, aluminum chlorohydrate, aluminum zirconium tetrachlorohydrexglycine and mixtures thereof.

The cosmetic agents as contemplated herein can contain certain aluminum salts. It is therefore preferred within the scope of the present disclosure for the cosmetic agent to contain at least one aluminum salt selected from the group of (i) water-soluble inorganic salts of aluminum, in particular aluminum chlorohydrate, aluminum sesquichlorohydrate, aluminum dichlorohydrate, aluminum hydroxide, potassium aluminum sulfate, aluminum bromide hydrate, aluminum chloride, aluminum sulfate; (ii) water-soluble organic salts of aluminum, in particular aluminum chlorohydrex propylene glycol, aluminum chlorhydrex polyethylene glycol, aluminum propylene glycol complexes, aluminum sesquichlorohydrex propylene glycol, aluminum sesquichlorohydrex polyethylene glycol, aluminum propylene glycol dichlorohydrex, aluminum polyethylene glycol dichlorohydrex, aluminum undecylenoyl collagen amino acid, sodium aluminum lactate, sodium aluminum chlorohydroxy lactate, aluminum lipoamino acids, aluminum lactate, aluminum chlorohydroxyallantoinate, sodium aluminum chlorohydroxylactate; and (iii) mixtures thereof.

Furthermore, the cosmetic agents as contemplated herein can contain special aluminum-zirconium salts. Preferred embodiments are therefore wherein the cosmetic agent contains at least one aluminum-zirconium salt selected from the group of (i) water-soluble inorganic aluminum-zirconium salts, in particular aluminum zirconium trichlorohydrate, aluminum zirconium tetrachlor hydrate, aluminum zirconium pentachlorohydrate, aluminum zirconium octachlorhydrate; (ii) water-soluble organic aluminum-zirconium salts, in particular aluminum zirconium-propylene glycol complexes, aluminum zirconium trichlorohydrexglycine, aluminum zirconium tetrachlorohydrexglycine, aluminum zirconium pentachlorohydrexglycine, aluminum zirconium octachlorohydrexglycine; and (iii) mixtures thereof.

As contemplated herein, the terms "aluminum salts" and "aluminum-zirconium salts" are not to be understood as meaning aluminosilicates and zeolites. Furthermore, as contemplated herein, water-soluble aluminum salts or water-soluble aluminum-zirconium salts are understood to mean those salts which have a solubility of at least about 3% by weight at 20° C., i.e., at least 3 g of the antiperspirant aluminum salt or aluminum-zirconium salt dissolves in 97 g of water at 20° C.

Particularly preferred inorganic aluminum salts are selected from aluminum chlorohydrate, in particular aluminum chlorohydrate, having the general formula $[Al_2(OH)_5Cl.1-6H_2O]_n$, $[Al_2(OH)_5Cl.2-3H_2O]_n$, which may be present in the non-activated (polymerized) or in activated (depolymerized) form, and aluminum chlorohydrate having the general formula $[Al_2(OH)_4Cl_2.1-6H_2O]_n$, preferably $[Al_2(OH)_4Cl_2.2-3H_2O]_n$, which may be in unactivated (polymerized) or in activated (depolymerized) form.

Particularly preferred antiperspirant aluminum salts as contemplated herein are selected from so-called "activated" aluminum salts, which are also referred to as antiperspirant active ingredients "with enhanced activity". Activated aluminum salts are generally produced by heat treatment of a dilute solution of the corresponding salt (e.g., a solution containing 10% by weight salt) in order to increase its HPLC peak 4 to peak 3 area ratio. The activated salt can then be dried to a powder, in particular spray-dried. Drying the roller is also suitable in addition to spray-drying. Activated aluminum salts typically have an HPLC peak 4 to peak 3 area ratio of at least about 0.4, preferably at least about 0.7, more preferably at least about 0.9, wherein at least about 70% of the aluminum is attributed to these HPLC peaks.

In this context, "activated" aluminum zirconium salts are also known which have a high HPLC peak 5 aluminum content, in particular a peak 5 area of at least about 33%, preferably of at least about 45%, based on the total area under the peaks from about 2 to about 5 as measured by HPLC of a 10% by weight aqueous solution of the active ingredient under conditions in which the aluminum species are dissolved in at least about 4 successive peaks (indicated by peaks 2 to 5). Preferred aluminum zirconium salts having a high HPLC peak 5 aluminum content are also referred to as "$E^5AZCH$". Furthermore, the activated aluminum-zirconium salt mentioned above can additionally be stabilized with a water-soluble strontium salt and/or with a water-soluble calcium salt.

It is also possible as contemplated hereinto use antiperspirant aluminum salts as non-aqueous solutions or solubilisates of an activated antiperspirant aluminum or aluminum-zirconium salt. Such aluminum or aluminum zirconium salts are stabilized against loss of activation of the salt by the addition of an effective amount of a polyhydric alcohol having 3 to 6 carbon atoms and from about 3 to about 6 hydroxyl groups, preferably propylene glycol, sorbitol and pentaerythritol.

Particular preference is also given to complexes of activated antiperspirant aluminum or aluminum-zirconium salts with a polyhydric alcohol which contains from about 20 to about 50% by weight, preferably from about 20 to about 42% by weight, of the activated antiperspirant aluminum or aluminum-zirconium salt and from about 2 to about 16% by weight of molecularly bound water, wherein the remainder is 100% by weight of at least one polyhydric alcohol having from about 3 to about 6 carbon atoms and from about 3 to about 6 hydroxyl groups. Propylene glycol, propylene glycol/sorbitol mixtures and propylene glycol/pentaerythritol mixtures are such preferred alcohols.

Within the scope of the present disclosure, it is also possible to use basic calcium-aluminum salts as antiperspirant aluminum salts. These salts can be obtained by converting calcium carbonate with aluminum chlorohydroxide or aluminum chloride and aluminum powder, or by adding calcium chloride dihydrate to aluminum chlorohydroxide. However, aluminum-zirconium complexes are also possible, which are buffered with salts of amino acids, in particular with alkali metal and alkaline earth diglycinates.

Aluminum or aluminum-zirconium salts, which are preferably stabilized by amino acids, in particular glycine, hydroxyalkanoic acids, in particular glycolic acid and lactic acid, or betaines, can also be used as the antiperspirant-activated aluminum and aluminum-zirconium salts which are preferred as contemplated herein.

Furthermore, preferred activated aluminum salts are those of the general formula $Al_2(OH)_{6-a}Xa$, wherein X stands for Cl, Br, I or $NO_3$ and "a" is a number from about 0.3 to about 5, preferably from about 0.8 to about 2.5, in particular from about 1 to about 2, so that the molar ratio of Al:X is from about 0.9:1 to about 2.1:1. Particularly preferred is aluminum chlorohydrate (i.e., X stands for Cl for the aforementioned formula) and especially 5/6 basic aluminum chlorohydrate with "a"=1 so that the molar ratio of aluminum to chlorine is from about 1.9:1 to about 2.1:1.

Preferred activated aluminum zirconium salts are those of the general formula $ZrO(OH)_{2-pb}Y_b$, wherein Y stands for Cl, Br, I, $NO_3$ or $SO_4$, b is a rational number from about 0.8 to about 2 and p is the valency of Y, so that the Al:Zr molar ratio is from about 2 to about 10 and the metal:(X+Y) ratio is from about 0.73 to about 2.1, preferably from about 0.9 to about 1.5. A particularly preferred salt is aluminum zirconium chlorohydrate (i.e., X and Y stand for Cl) which has an Al:Zr ratio of from about 2 to about 10 and a molar metal:Cl ratio of from about 0.9 to about 2.1.

Particularly preferred antiperspirant aluminum salts as contemplated hereinhave a molar metal-to-chloride ratio of from about 1.9 to about 2.1. The metal-to-chloride ratio of aluminum sesquichlorohydrates which are also particularly preferred as contemplated herein is from about 1.5:1 to about 1.8:1. Preferred aluminum zirconium tetrachlorohydrates have a molar ratio of Al:Zr of from about 2 to about 6 and of metal:chloride of from about 0.9 to about 1.3, wherein particular preference is given to salts having a molar metal-to-chloride ratio of from about 0.9 to about 1.1, preferably from about 0.9 to about 1.0.

In the context of the present disclosure, it is preferred if certain of the active ingredients mentioned above are used. Preferred embodiments of the present disclosure are therefore wherein the cosmetic agent contains at least one first active ingredient selected from the group of triethyl citrate, 3-[(2-ethylhexyl)oxy]-1,2-propanediol, 2-benzylheptanol, phenoxyethanol, cocamidopropyl PG dimonium chloride phosphate, 1,2-hexanediol, 1,2-octanediol, 1,2-decanediol, tropolone, silver lactate, magnesium oxide, aluminum chlorohydrate, aluminum zirconiumtetrachlorohydrexglycine and mixtures thereof. The use of these active ingredients has proven to be particularly advantageous with respect to the deodorizing and/or antiperspirant performance. In particular, a synergistic increase in the deodorizing and/or antiperspirant performance is achieved. In addition, the use of these active ingredients can be used to further increase both the skin compatibility and the cosmetic properties of the agents as contemplated herein. These compounds have the following chemical names and CAS numbers:

| Preservative | Chemical name/Structural formula | CAS number |
| --- | --- | --- |
| Triethylcitrate | 2-hydroxypropane-1,2,3-tricarboxylic acid triethyl ester | 77-93-0 |
| 3-[(2-ethylhexyl)oxy]-1,2-propanediol | OCTOXYGLYCERIN | 70445-33-9 |
| 2-benzylheptanol | 2-benzyl-1-heptanol | 92368-90-6 |
| Phenoxyethanol | 2-phenoxy-1-ethanol | 122-99-6 |
| Cocamidopropyl PG | Propanaminium, 2,3-dihydroxy-N,N- | 83682-78-4 |

| Preservative | Chemical name/Structural formula | CAS number |
| --- | --- | --- |
| dimonium chloride phosphate | dimethyl-N-(coconut-alkyl)-, 3-sodium hydrogen phosphate ester, chloride | |
| 1,2-hexanediol | $CH_3(CH_2)_3CH(OH)CH_2OH$ | 6920-22-5 |
| 1,2-octanediol | $CH_3(CH_2)_5CH(OH)CH_2OH$ | 1117-86-8 |
| 1,2-decanediol | $CH_3(CH_2)_7CH(OH)CH_2OH$ | 1119-86-4 |
| Tropolone | 2-hydroxy-2,4,6-cycloheptatriene-1-one | 38768-08-0 |
| Silver lactate | Silver lactate | 128-00-7 |
| Magnesium oxide | Magnesium oxide, MgO | 1309-48-4 |
| Aluminum chlorohydrate | Aluminum chloride, basic | 1327-41-9 |
| Aluminum zirconium tetrachlorohydrex glycine | $Al_4Zr(OH)_{12}Cl_4Gly \times nH_2O$ | 90604-80-1 |

The deodorizing and/or antiperspirant effect can be further increased when the cosmetic agents contain more than one of the active ingredients mentioned above. Preferred cosmetic agents are therefore wherein they contain at least two active ingredients selected from the group of triethyl citrate, 3-[(2-ethylhexyl)oxy]-1,2-propanediol, 2-benzylheptanol, phenoxyethanol, cocamidopropyl PG dimonium chloride phosphate, 1,2-hexanediol, 1,2-octanediol, 1,2-decanediol, tropolone, silver lactate, magnesium oxide, aluminum chlorohydrate, aluminum zirconium tetrachlorohydrexglycine and mixtures thereof.

Further preferred cosmetic agents as contemplated herein are wherein they contain at least three active ingredients selected from the group of triethyl citrate, 3-[(2-ethylhexyl)oxy]-1,2-propanediol, 2-benzylheptanol, phenoxyethanol, cocamidopropyl PG dimonium chloride phosphate, 1,2-hexanediol, 1,2-octanediol, 1,2-decanediol, tropolone, silver lactate, magnesium oxide, aluminum chlorohydrate, aluminum zirconium tetrachlorohydrexglycine and mixtures thereof.

The cosmetic agents as contemplated herein preferably contain the active ingredient(s) mentioned above in certain amounts. Preferred cosmetic agents as contemplated herein are therefore wherein they comprise, based on their total weight, from about 0.0005 to about 35% by weight, preferably from about 0.005 to about 25% by weight, more preferably from about 0.01 to about 10% by weight, in particular from about 0.5 to about 8.0% by weight, of at least one active ingredient selected from the group of triethyl citrate, 3-[(2-ethylhexyl)oxy]-1,2-propanediol, 2-benzylheptanol, phenoxyethanol, cocamidopropyl PG dimonium chloride phosphate, 1,2-hexanediol, 1,2-octanediol, 1,2-decanediol, tropolone, silver lactate, magnesium oxide, aluminum chlorohydrate, aluminum zirconium tetrachlorohydrexglycine and mixtures thereof. The use of such amounts of the at least one active ingredient leads to a synergistic increase in the deodorizing and/or antiperspirant performance. As a result, the use quantity of active ingredients can be reduced without adversely affecting the deodorizing and/or antiperspirant performance. The cosmetic agents as contemplated herein are therefore particularly skin-friendly.

Through the high-performance combination as contemplated herein, the agents as contemplated herein can also be formulated without the use of aluminum salts without any performance losses. The effectiveness against body odor is generally comparatively low in the case of products which are free from aluminum, wherein the performance deficiency becomes noticeable particularly after from about 24 to about 48 hours. The combination as contemplated herein achieves a significant improvement in deodorizing performance in the period from about 24 to about 48 hours after administration.

Preferred cosmetic agents as contemplated herein, wherein they are free from aluminum salts.

As a further component, the cosmetic agents as contemplated herein can contain at least one active ingredient selected from the group of cetylpyridinium chloride, benzalkonium chloride, benzethonium chloride, zinc hydroxide carbonate, zinc phenolsulfonate, polyglyceryl-2 caprate, sorbitanancaprylate, octenidine, charnesolic acid, tartaric acid and mixtures thereof. Preferred cosmetic agents as contemplated herein additionally include one or more active ingredients selected from the group of cetylpyridinium chloride, benzalkonium chloride, benzethonium chloride, zinc hydroxide carbonate, zinc phenolsulfonate, polyglyceryl-2 caprate, sorbitanancaprylate, octenidine, charnesolic acid, tartaric acid and mixtures thereof.

Within the scope of the present disclosure, it is preferred if certain active ingredients are used. Preferred embodiments of the present disclosure are therefore wherein the cosmetic agent contains at least one further active ingredient selected from the group of cetylpyridinium chloride, benzalkonium chloride, benzethonium chloride, zinc hydroxide carbonate, zinc phenolsulfonate, polyglyceryl-2 caprate, sorbitanancaprylate, octenidine, charnesolic acid, tartaric acid and mixtures thereof.

These compounds have the following chemical names and CAS numbers:

| Preservative | Chemical name/Structural formula | CAS number |
| --- | --- | --- |
| Cetylpyridinium chloride | 1-hexadecylpyridinium chloride | 123-03-5 |
| Benzalkonium chloride | N-$C_8$—$C_{18}$-alkyl-N-benzyl-N,N-dimethyl ammonium chloride | 8001-54-5 |
| Benzethonium chloride | Diisobutylphenoxyethoxyethyldimethyl-benzyl ammonium chloride | 121-54-0 |
| Zinc hydroxide carbonate | $[ZnCO_3]_2*[Zn(OH)_2]_3$ | 2/5/5263 |
| Zinc phenolsulfonate | Zinc phenolsulfonate | 127-82-2 |

| Preservative | Chemical name/Structural formula | CAS number |
| --- | --- | --- |
| Polyglyceryl-2 caprate | 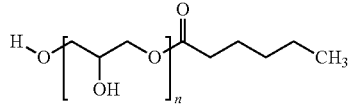

n = 2 | 156153-06-9 |
| Sorbitan caprylate | Sorbitan monooctanoate | 60177-36-8 |
| Octenidine | N-octyl-1-[10-(4-octyliminopyridine-1-yl)decyl]pyridine-4-imine dihydrochloride | 70775-75-6 |
| Charnesolic acid | (4aR, 10aS)-5,6-dihydroxy-1,1-dimethyl-7-propan-2-yl-2,3,4,9,10,10a-hexahydro-phenanthrene-4a-carboxylic acid | 9/7/3650 |
| Tartaric acid | D- and/or L-tartaric acid | 133-37-9 |

The deodorizing and/or antiperspirant effect can be further increased when the cosmetic agents contain more than one of the active ingredients mentioned above. Preferred cosmetic agents are therefore wherein they contain at least two active ingredients selected from the group of cetylpyridinium chloride, benzalkonium chloride, benzethonium chloride, zinc hydroxide carbonate, zinc phenolsulfonate, polyglyceryl-2 caprate, sorbitanancaprylate, octenidine, charnesolic acid, tartaric acid and mixtures thereof.

Further preferred cosmetic agents as contemplated herein are wherein they contain at least three active ingredients selected from the group of cetylpyridinium chloride, benzalkonium chloride, benzethonium chloride, zinc hydroxide carbonate, zinc phenolsulfonate, polyglyceryl-2 caprate, sorbitanancaprylate, octenidine, charnesolic acid, tartaric acid and mixtures thereof.

The cosmetic agents as contemplated herein preferably contain the second active ingredient in certain ranges of amounts. Preferred cosmetic agents as contemplated herein are therefore wherein they, based on their total weight, contain from about 0.001 to about 20% by weight, preferably from about 0.005 to about 15% by weight, more preferably from about 0.01 to about 10% by weight, in particular from about 0.05 to about 10% by weight, of at least one further active ingredient selected from the group of cetylpyridinium chloride, benzalkonium chloride, benzethonium chloride, zinc hydroxide carbonate, zinc phenolsulfonate, polyglyceryl-2 caprate, sorbitanancaprylate, octenidine, charnesolic acid, tartaric acid and mixtures thereof.

The cosmetic agents as contemplated herein can additionally contain additional deodorant active ingredients (C). However, the additional deodorant active ingredient (C) is different from the first active ingredient (A) and the second active ingredient (B).

It can be preferred for the purposes of the present disclosure if the cosmetic agent additionally contains a deodorant active ingredient (C). Preferred agents are therefore wherein they additionally contain at least one deodorant active ingredient (C) selected from the group of (i) active ingredients against exoesterases, in particular against arylsulfatase, lipase, beta-glucuronidase and cystathione-β-lyase; (ii) odor absorbers, in particular silicates, such as montmorillonite, kaolinite, ilite, beidellite, nontronite, saponite, hectorite, bentonite, smectite and talcum, zeolites, zincricinoleate, cyclodextrins; (iii) deodorant ion exchangers; (iv) microbe-inhibiting agents; (v) prebiotically active components; and (vi) mixtures thereof.

Silicates are used as odor absorbers, which at the same time can also advantageously support the rheological properties of the cosmetic agents as contemplated herein. Particularly advantageous silicates include, in particular, layer silicates and, among these, in particular montmorillonite, kaolinite, ilite, beidellite, nontronite, saponite, hectorite, bentonite, smectite and talcum. Further advantageous odor absorbers are, for example, zeolites, zinc ricinoleate, cyclodextrins, certain metal oxides, e.g., alumina, and chlorophyll.

Furthermore, the deodorant active ingredient can be selected from the group of terpene alcohols, such as farnesol, chlorophyll-copper complexes, carboxylic acid esters, in particular carboxylic acid monoesters of mono-, di- and triglycerol (in particular glycerol monolaurate, diglycerol monocaprinate, diglycerol monolaurate, triglycerol monolaurate and triglycerol monomyristate) and plant extracts (e.g., green tea and ingredients of lime blossom oil).

Further preferred deodorant active ingredients are selected from so-called prebiotically active components, which as contemplated herein are to be understood to mean those components which only or at least predominantly inhibit the odor-forming microbes of the skin microflora, but not the desired, that is, the non-odor-forming microbes. To be mentioned here explicitly are needle tree extracts, in particular from the group of the Pinaceae, and plant extracts from the group of the Sapindaceae, Araliaceae, Lamiaceae and Saxifragaceae, in particular extracts from *Picea* spp., *Paullinia* sp., *Panax* sp., *Lamium album* or *Ribes nigrum*, and mixtures of these substances.

Further preferred deodorant active ingredients are selected from the microbe-inhibiting acting perfume oils and the deosafe perfume oils which are obtainable from Symrise, formerly Haarmann and Reimer.

The enzyme inhibitors include substances which inhibit the enzymes responsible for the sweat decomposition, in particular arylsulfatase, β-glucuronidase, aminoacylase, the ester-cleaving lipases and the lipoxigenases, e.g., zinc glycinate.

The at least one further deodorant active ingredient (C) is preferably used in the cosmetic products as contemplated herein in certain ranges of amounts. It is therefore preferred in this context if, based on their total weight, they contain from about 0.005 to about 20% by weight, preferably from about 0.1 to about 15% by weight, more preferably from about 0.1 to about 13% by weight, in particular from about 0.1 to about 10% by weight of at least one deodorant active ingredient (C). If a mixture of deodorant active ingredients is used, the quantities mentioned above relate to the amount specification listed above for the mixture of these active ingredients.

Within the scope of the present disclosure it may be provided that, in addition to the additional deodorant active ingredients mentioned above, the cosmetic agents as contemplated herein contain further ingredients selected from the group of (i) waxes; (ii) emulsifiers and/or surfactants; (iii) hydrogeling agents; (iv) skin-cooling active ingredients; (v) propellants; (vi) thickeners, and (vii) mixtures thereof.

The cosmetic agents as contemplated herein can additionally contain at least one wax. In the context of the present disclosure, the term "waxes" is understood to mean substances which are kneadable or solid to brittle hard at 20° C., have a coarse to finely crystalline structure and are color-translucent to opaque, but not glassy. Furthermore, these substances melt above 25° C. without decomposition, are slightly liquid (slightly viscous) slightly above the melting point, have a strongly temperature-dependent consistency and solubility and are polishable under slight pressure. It is therefore advantageous as contemplated herein if the cosmetic agent additionally contains at least one wax selected from the group of (i) coconut fatty acid glycerol mono-, di- and triesters; (ii) Butyrospermum Parkii (shea butter); (iii) esters of saturated monohydric $C_{8-18}$ alcohols with saturated $C_{12-18}$ monocarboxylic acids; (iv) linear, primary $C_{12}$-$C_{24}$ alkanols; (v) esters of a saturated monohydric $C_{16}$-$C_{60}$ alkanol and a saturated $C_8$-$C_{36}$ monocarboxylic acid, in particular cetyl behenate, stearyl behenate and $C_{20}$-$C_{40}$ alkyl stearate; (vi) glycerol triesters of saturated linear $C_{12}$-$C_{30}$ carboxylic acids which may be hydroxylated, in particular hydrogenated palm oil, hydrogenated coconut oil, hydrogenated castor oil, glyceryl tribehenate and glyceryltri-12-hydroxystearate; (vii) natural vegetable waxes, in particular candelilla wax, carnauba wax, Japan wax, sugar cane wax, ouricoury wax, cork wax, sunflower wax, fruit waxes; (viii) animal waxes, in particular bee wax, shellac wax and sperm; (ix) synthetic waxes, in particular montanester waxes, hydrogenated jojoba waxes and sasol waxes, polyalkylene waxes and polyethylene glycol waxes, $C_{20}$-$C_{40}$ dialkyl esters of dimer acids, $C_{30-50}$ alkyl bee waxes and alkyl and alkyl aryl esters of dimer fatty acids, paraffin waxes; and (x) their mixtures. The cosmetic agent contains the additional at least one wax preferably in a total amount of from about 0.01 to about 20% by weight, more preferably from about 3 to about 20% by weight, even more preferably from about 5 to about 18% by weight, in particular from about 6 to about 15% by weight, based on the total weight of the cosmetic agent.

Emulsifiers and surfactants which are preferred as contemplated herein are selected from anionic, cationic, nonionic, amphoteric, in particular ampholytic and zwitterionic emulsifiers and surfactants. Surfactants are amphiphilic (bi-functional) compounds which consist of at least one hydrophobic and at least one hydrophilic molecular component. The hydrophobic radical is preferably a hydrocarbon chain having from about 8 to about 28 carbon atoms, which can be saturated or unsaturated, linear or branched. This $C_8$-$C_{28}$ alkyl chain is particularly preferably linear.

Anionic surfactants are understood to mean surfactants with exclusively anionic charges; they contain, e.g., carboxyl groups, sulfonic acid groups or sulfate groups. Particularly preferred anionic surfactants are alkyl sulfates, alkyl ether sulfates, acyl glutamates and $C_{8-24}$ carboxylic acids and salts thereof, the so-called soaps.

Cationic surfactants are understood to mean surfactants with exclusively cationic charges; they contain, e.g., quaternary ammonium groups. Preference is given to cationic surfactants of the quaternary ammonium compound type, the esterquats and the amidoamines. Preferred quaternary ammonium compounds are ammonium halides and the imidazolium compounds known under the INCI names Quaternium-27 and Quaternium-83. Other cationic surfactants which can be used as contemplated herein are the quaternized protein hydrolysates. Preferred esterquats are quaternized ester salts of fatty acids with triethanolamine, quaternized ester salts of fatty acids with diethanolalkylamines and quaternized ester salts of fatty acids with 1,2-dihydroxypropyldialkylamines.

The amphoteric surfactants are subdivided into ampholytic surfactants and zwitterionic surfactants. Ampholytic surfactants are understood to mean those surface-active compounds which have both acidic (for example —COOH or —SO$_3$H groups) and basic hydrophilic groups (for example amino groups) and thus, depending on the condition, have an acidic or basic behavior. The person skilled in the art understands zwitterionic surfactants to be surfactants which carry both a negative and a positive charge in the same molecule. Examples of preferred zwitterionic surfactants are the betaines, the N-alkyl-N,N-dimethylammonium glycinates, the N-acylaminopropyl N,N-dimethylammonium glycinates and the 2-alkyl-3-carboxymethyl-3-hydroxyethylimidazolines, in each case with from about 8 to about 24 carbon atoms in the alkyl group. Examples of preferred ampholytic surfactants are N-alkylglycines, N-alkylaminopropionic acids, N-alkylaminobutyric acids, N-alkyliminodipropionic acids, NH-hydroxyethyl-N-alkylamidopropylglycines, N-alkyltaurines, N-alkylsarcosines, 2-alkylaminopropionic acids and alkylaminoacetic acids each having 8 to 24 carbon atoms in the alkyl group The cosmetic agents as contemplated herein, which are formulated as an emulsion, in particular as an oil-in-water emulsion, preferably contain at least one nonionic oil-in-water emulsifier with an HLB value of more than from about 7 to about 20. These are emulsifiers which are generally known to a person skilled in the art. For ethoxylated products, the HLB value is calculated according to the formula HLB=(100−L): 5, wherein L is the weight fraction of the lipophilic groups, i.e., the fatty alkyl or fatty acyl groups, in the ethylene oxide adducts expressed as weight percent. In this context, it may be preferred as contemplated herein if a water-in-oil emulsifier with an HLB value of greater than 1.0 and less than or equal to 7.0 is used.

For the thickening of the cosmetic agents as contemplated herein, preference is given for using hydrogel-forming substances which are selected from cellulose ethers, primarily hydroxyalkyl celluloses, in particular hydroxypropylcellulose, hydroxypropylmethylcellulose, hydroxyethylcellulose, carboxymethylcellulose, cetylhydroxyethylcellulose, hydroxybutylmethylcellulose, methylhydroxyethylcellulose, furthermore xanthan gum, sclerotium gum, succinoglucans, polygalactomannans, in particular guar gums and locust bean gum, and in particular guar gum and locust bean gum itself and the nonionic hydroxyalkylguar derivatives and locust bean gum derivatives such as hydroxypropylguar, carboxymethylhydroxypropylguar, hydroxypropylmethylguar, hydroxyethylguar and carboxymethylguar, furthermore pectins, agar, carrageenan, tragacanth, gum arabic, karaya gum, tarag gum, gellan, gelatin, casein, propylene glycol alginate, alginic acids and their salts, in particular sodium alginate, potassium alginate and calcium alginate, furthermore polyvinylpyrrolidones, polyvinyl alcohols, polyacrylamides. Particularly preferred hydrogel formers are selected from cellulose ethers, primarily from hydroxyalkylcelluloses, in particular from hydroxypropylcellulose, hydroxypropylmethylcellulose, hydroxyethylcellulose, carboxymethylcellulose, cetylhydroxyethylcellulose, hydroxybutylmethylcellulose and methylhydroxyethylcellulose, and mixtures thereof. However, a lipophilic thickener can also be used. Preferred lipophilic thickeners as contemplated herein are selected from hydrophobicized clay minerals and pyrogenic silicas.

The cosmetic agents as contemplated herein can additionally contain at least one skin-cooling active ingredient. Suitable skin-cooling active ingredients as contemplated herein are, for example, menthol, isopulegol and menthol derivatives, e.g., menthyl lactylate, menthylglycolate, menthyl ethyl oxamate, menthylpyrrolidonecarboxylic acid, menthylmethyl ether, menthoxypropanediol, menthonglycerol acetal (9-methyl-6-(1-methylethyl)-1,4-dioxaspiro (4,5) decan-2-methanol), monomenthylsuccinate, 2-hydroxymethyl-3,5,5-trimethylcyclohexanol and 5-methyl-2-1-methylethyl)cyclohexyl-N-ethyl oxamate. Preferred as skin-cooling active ingredients are menthol, isopulegol, menthyllactate, menthoxypropanediol, menthylpyrrolidonecarboxylic acid and 5-methyl-2-(1-methylethyl) cyclohexyl-N-ethyloxamate, and mixtures of these substances, in particular mixtures of menthol and menthyl lactate, menthol, mentholglycolate and menthyl lactate, menthol and menthoxypropanediol or menthol and isopulegol.

Furthermore, it may be provided that the cosmetic agents as contemplated herein contain a propellant. In this case, they are assembled as a propellant-driven aerosol. Preferred propellants (propellant gases) are propane, propene, n-butane, isobutane, isobutene, n-pentane, pentene, isopentane, isopentene, methane, ethane, dimethyl ether, nitrogen, air, oxygen, nitrous oxide, 1,1,1,3-tetrafluoroethane, heptafluoro-n-propane, perfluoroethane, monochlorodifluoromethane, 1,1-difluoroethane and tetrafluoropropenes, both individually and in their mixtures. Also, hydrophilic propellant gases such as, for example, carbon dioxide, can advantageously be used for the purposes of the present disclosure if the proportion of hydrophilic gases is selected to be small and lipophilic propellant gas (e.g., propane/butane) is present in excess. Particular preference is given to propane, n-butane, isobutane and mixtures of these propene gases. It has been found that the use of n-butane as the only propellant gas can be particularly preferred as contemplated herein. The total amount of the propellants is from about 20 to about 95% by weight, preferably from about 30 to about 85% by weight, in particular from about 40 to about 75% by weight, based in each case on the total weight of the cosmetic agent, of the above-described components a) and b) and optionally the additional active ingredients and substances and the propellant.

The cosmetic agent as contemplated herein can be applied by various methods. According to a first embodiment, the cosmetic agent is assembled as a spray application. The spray application is carried out by employing a spraying device which contains, in a container, a filling of the liquid, viscous, suspension-form or powder-form antiperspirant cosmetic agent as contemplated herein. The filling can be under the pressure of a propellant (pressurized gas cans, pressurized gas packs, aerosol packs), or it can be a mechanically operated pump atomizer without a propellant gas (pump spray/squeeze bottle). The containers have a removal device, preferably in the form of valves, which allow the removal of the contents as a mist, smoke, foam, powder, paste or liquid jet. Suitable containers for the spraying devices are, in particular, cylindrical vessels made of metal (aluminum, tinplate, space content preferably a maximum of 1,000 ml), protected or non-shattering glass or plastic (space content preferably a maximum of 220 ml) or shattering glass or plastic (space content preferably from about 50 to about 400 ml). Creamy, gel-like, pasty and liquid agents may be used, e.g. in pumping, spraying or squeezing dispensers, in particular also in multi-chamber pump, multi-chamber spray or multi-chamber squeezing dispensers. The packaging for the agents as contemplated herein can be opaque but also transparent or translucent.

According to a second embodiment, the cosmetic agent as contemplated herein can be assembled as a stick, soft solid, cream, roll-on, dibenzylidenalditol-based gel, loose or compact powder. The formulation of the cosmetic agents as contemplated herein in a particular dosage form, for example, an antiperspirant roll-on, an antiperspirant stick or an antiperspirant gel, is preferably directed to the requirements of the intended use. Depending on the intended use, the cosmetic agents as contemplated herein can therefore be present in solid, semi-solid, liquid, dispersible, emulsified, suspended, gel-shaped, multiphase or powder-like form. For the purposes of the present disclosure, the term "liquid" also encompasses any types of solid-state dispersions in liquids. Furthermore, polyphase cosmetic agents as contemplated herein, in the context of the present disclosure, are understood to mean those which have at least 2 different phases with a phase separation and in which the phases can be arranged horizontally, that is, one above the other, or vertically, that is next to each other.

The application can, for example, be carried out with a roll-ball applicator. Such rollers have a ball which is mounted in a ball-bed and which can be moved over a surface through movement. In this case, the ball receives some of the cosmetic agent as contemplated hereinto be distributed and conveys this to the surface to be treated. The packaging for these agents may be opaque, transparent or translucent, as noted above.

Furthermore, it is also possible to apply the cosmetic agents as contemplated herein by employing a solid stick in the form of a solid emulsion.

According to a third embodiment, the cosmetic agent as contemplated herein can be contained on and/or in a disposable substrate, selected from the group of cloths, pads and balls. Particular preference is given to wet wipes, i.e., which are prefabricated for the user, preferably individually packaged, as they are well known, e.g., from the field of glass cleaning or from the field of moist toilet paper. Such moist wipes, which can advantageously also contain preservatives, are impregnated or loaded with a cosmetic agent as contemplated herein and preferably packaged individually. For example, they can be used as a deodorant cloth, which is particularly interesting for use on the road. Preferred substrate materials are selected from porous sheet-like cloths. They may consist of a fibrous or cellular flexible material which has sufficient mechanical stability and, at the same time, softness for application to the skin. These wipes include wipes of woven and nonwoven synthetic and natural fibers, felt, paper or foam, such as hydrophilic polyurethane foam. Preferred deodorizing or antiperspirant substrates as contemplated herein can be obtained by soaking or impregnation or also by melting a cosmetic agent as contemplated hereinonto a substrate.

A second object of the present disclosure is a non-therapeutic cosmetic method for preventing and/or reducing body odor caused by perspiration and/or the perspiration of the body, in which a cosmetic agent as contemplated herein is applied to the skin, in particular to the skin of the armpits, and remains on the skin for at least about 1 hour, preferably for at least about 2 hours, more preferably for at least about 4 hours, in particular for at least about 6 hours.

With regard to further preferred embodiments of the method as contemplated herein, in particular with regard to the cosmetic agents used there, necessary changes being made applies to the statements regarding cosmetic agents as contemplated herein.

Finally, another object of the present disclosure is the use of a cosmetic agent as contemplated herein for preventing and/or reducing body odor of the body caused by perspiration.

With regard to further preferred embodiments of the use as contemplated herein, in particular with regard to the cosmetic agents used, the statements regarding the cosmetic agents as contemplated herein and the method as contemplated herein apply all necessary changes being made.

EXAMPLES

1. Deodorant Roll on with Alcohol

|  | 1A wt % | 1B wt % | 1C wt % | 1D wt % |
|---|---|---|---|---|
| Hydroxyethyl cellulose | 0.4 | 0.4 | 0.4 | 0.4 |
| 2-butyl octanoic acid | 0.3 | 0.5 | 0.7 | 0.4 |
| Polyglyceryl-3 caprylate | 0.4 | 0.2 | 0.1 | 0.5 |
| Phenoxyethanol | 0.5 | 0.5 | 0.5 | 0.5 |
| Triethyl citrates | 1.0 | 1.0 | 1.0 | 1.0 |
| Ethanol (96%) | 30.0 | 30.0 | 30.0 | 30.0 |
| Ceteareth-12 | 2.0 | 2.0 | 2.0 | 2.0 |
| Ceteareth-30 | 2.0 | 2.0 | 2.0 | 2.0 |
| Perfume | 1.0 | 1.0 | 1.0 | 1.0 |
| Water | Ad 100 | Ad 100 | Ad 100 | Ad 100 |

2. Deodorant Roll without Alcohol

|  | 2A wt % | 2B wt % | 2C wt % | 2D wt % |
|---|---|---|---|---|
| PPG-15 stearyl ether | 0.5 | 0.5 | 0.5 | 0.5 |
| Steareth-2 | 2.4 | 2.4 | 2.4 | 2.4 |
| Steareth-21 | 1.5 | 1.5 | 1.5 | 1.5 |
| 2-butyl octanoic acid | 0.3 | 0.5 | 0.7 | 0.4 |
| Polyglyceryl-3 caprylate | 0.4 | 0.2 | 0.1 | 0.5 |
| Phenoxyethanol | 0.5 | 0.5 | 0.5 | 0.5 |
| EDETA BX Powder | 0.1 | 0.1 | 0.1 | 0.1 |
| Perfume | 1.0 | 1.0 | 1.0 | 1.0 |
| Water | Ad 100 | Ad 100 | Ad 100 | Ad 100 |

3. Deodorant Atomizer

|  | 3A wt % | 3B wt % | 3C wt % | 3D wt % |
|---|---|---|---|---|
| PEG-40 hydrogenated castor oil | 0.5 |  |  |  |
| 2-butyl octanoic acid | 0.3 | 0.5 | 0.7 | 0.4 |
| Polyglyceryl-3 caprylate | 0.4 | 0.2 | 0.1 | 0.5 |
| Triethyl citrates | 3.0 | 3.0 | 3.0 | 3.0 |
| Ethanol (96%) | 55.0 | 55.0 | 55.0 | 55.0 |
| Perfume | 1.0 | 1.0 | 1.0 | 1.0 |
| Water | Ad 100 | Ad 100 | Ad 100 | Ad 100 |

4. Deodorant Aerosol

|  | 4-1 | 4-2 | 4-3 | 4-4 |
|---|---|---|---|---|
| Ethanol 96% | 88.5 | 88.5 | 88.4 | 88.3 |
| 2-butyl octanoic acid | 0.3 | 0.5 | 0.7 | 0.4 |
| Polyglyceryl-3 caprylate | 0.4 | 0.2 | 0.1 | 0.5 |
| Triethyl citrates | 6.0 | 6.0 | 6.0 | 6.0 |
| Phenoxyethanol | 0.8 | 0.8 | 0.8 | 0.8 |
| Perfume | 4.0 | 4.0 | 4.0 | 4.0 |

The formulations are filled into aerosol dispensers in a weight ratio of 1:3 using the propellant propane/butane (15/85).

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

The invention claimed is:
1. A cosmetic agent consisting of:
   from about 88.3 to about 88.5% by weight of ethanol, based on the total weight of the cosmetic agent;
   from about 0.3 to about 0.7% by weight of 2-butyl octanoic acid, based on the total weight of the cosmetic agent;
   from about 0.1 to about 0.5% by weight of polyglyceryl-3 caprylate, based on the total weight of the cosmetic agent;
   about 6% by weight of triethyl citrate(s), based on the total weight of the cosmetic agent;
   about 0.8% by weight of phenoxyethanol, based on the total weight of the cosmetic agent; and
   about 4% by weight of perfume, based on the total weight of the cosmetic agent, wherein the cosmetic agent is in combination with a propellant as a deodorant aerosol.
2. A cosmetic agent consisting of:
   about 0.4 by weight of hydroxyethyl cellulose, based on the total weight of the cosmetic agent;
   from about 0.3 to about 0.7% by weight of 2-butyl octanoic acid, based on the total weight of the cosmetic agent;
   from about 0.1 to about 0.5% by weight of polyglyceryl-3 caprylate, based on the total weight of the cosmetic agent;
   about 0.5% by weight of phenoxyethanol, based on the total weight of the cosmetic agent;
   about 1% by weight of triethyl citrate(s), based on the total weight of the cosmetic agent;
   about 30% by weight of ethanol, based on the total weight of the cosmetic agent;
   about 2% by weight of Ceteareth-12, based on the total weight of the cosmetic agent;
   about 2% by weight of Ceteareth-30, based on the total weight of the cosmetic agent;
   about 1% by weight of perfume, based on the total weight of the cosmetic agent; and
   remainder of the cosmetic agent by weight of water, based on the total weight of the cosmetic agent, wherein the cosmetic agent is a deodorant.
3. A cosmetic agent consisting of:
   from about 0 to about 0.5 by weight of PPG-40 hydrogenated castor oil, based on the total weight of the cosmetic agent;
   from about 0.3 to about 0.7% by weight of 2-butyl octanoic acid, based on the total weight of the cosmetic agent;

from about 0.1 to about 0.5% by weight of polyglyceryl-3 caprylate, based on the total weight of the cosmetic agent;

about 3% by weight of triethyl citrates, based on the total weight of the cosmetic agent;

about 55% by weight of ethanol, based on the total weight of the cosmetic agent;

about 1% by weight of perfume, based on the total weight of the cosmetic agent; and remainder of the cosmetic agent by weight of water, based on the total weight of the cosmetic agent, wherein the cosmetic agent is a deodorant.

* * * * *